(12) United States Patent
Dreyer et al.

(10) Patent No.: US 8,154,727 B2
(45) Date of Patent: Apr. 10, 2012

(54) HOLLOW WAVEGUIDE CAVITY RINGDOWN SPECTROSCOPY

(75) Inventors: Chris Dreyer, Lakewood, CO (US); Greg S. Mungas, Arcadia, CA (US)

(73) Assignee: Colorado School of Mines, Golden, CO (US)

( * ) Notice: Subject to any disclaimer, the term of this patent is extended or adjusted under 35 U.S.C. 154(b) by 783 days.

(21) Appl. No.: 12/041,648

(22) Filed: Mar. 3, 2008

(65) Prior Publication Data

US 2009/0059234 A1    Mar. 5, 2009

Related U.S. Application Data

(60) Provisional application No. 60/892,762, filed on Mar. 2, 2007.

(51) Int. Cl.
*G01N 21/00*    (2006.01)
(52) U.S. Cl. .......................... 356/437; 356/432; 356/436
(58) Field of Classification Search ........................ None
See application file for complete search history.

(56) References Cited

U.S. PATENT DOCUMENTS

| | | | |
|---|---|---|---|
| 4,793,709 A | 12/1988 | Jabr et al. | |
| 5,528,040 A | 6/1996 | Lehmann | |
| 5,912,740 A | 6/1999 | Zare et al. | |
| 6,172,823 B1 * | 1/2001 | Lehmann et al. | 359/834 |
| 6,768,548 B2 * | 7/2004 | Zare et al. | 356/432 |
| 6,795,190 B1 | 9/2004 | Paul et al. | |
| 6,839,140 B1 * | 1/2005 | O'Keefe et al. | 356/436 |
| 7,079,240 B2 * | 7/2006 | Scherer et al. | 356/318 |
| 7,768,647 B2 * | 8/2010 | Reeve et al. | 356/437 |
| 2002/0097401 A1 | 7/2002 | Malecki et al. | |
| 2006/0227331 A1 * | 10/2006 | Vollmer et al. | 356/483 |
| 2008/0111077 A1 * | 5/2008 | Miller | 250/339.07 |
| 2009/0232442 A1 * | 9/2009 | Loock et al. | 385/12 |
| 2010/0002993 A1 * | 1/2010 | Hasman | 385/31 |

\* cited by examiner

*Primary Examiner* — Tarifur Chowdhury
*Assistant Examiner* — Gordon Stock, Jr.
(74) *Attorney, Agent, or Firm* — Sheridan Ross P.C.

(57) ABSTRACT

Laser light is confined in a hollow waveguide between two highly reflective mirrors. This waveguide cavity is used to conduct Cavity Ringdown Absorption Spectroscopy of loss mechanisms in the cavity including absorption or scattering by gases, liquid, solids, and/or optical elements.

23 Claims, 8 Drawing Sheets

HOLLOW WAVEGUIDE CAVITY RINGDOWN SPECTROSCOPY

This application claims priority from U.S. Provisional Patent Application No. 60/892,762 filed Mar. 2, 2007, the disclosure of which is hereby incorporated herein by reference.

The U.S. Government has a paid-up license in this invention and the right in limited circumstances to require the patent owner to license others on reasonable terms as provided for by the terms of Grant Number NNG04GN40G awarded by NASA.

FIELD OF THE INVENTION

This invention relates generally to gas concentration measurement by laser light absorption, laser absorption cavity ringdown spectroscopy, and more particularly to the design, manufacturing, and use of a hollow waveguide cavity ringdown spectroscopy gas sensing instrument.

BACKGROUND

Gas concentration measurement by light absorption makes use of the nature of molecular and atomic gases to absorb portions of the electromagnetic spectrum that correspond to energy transitions of the absorbing gas species. There are several methods for using light absorption to measure gas concentration of species in a gas mixture.

Cavity ringdown spectroscopy (CRDS) is a gas sensing technique in which an optical cavity is formed by two or more highly reflective mirrors. Typically, CRDS-based measurements can provide 10-1000 times improvement in sensitivity compared to more conventional absorption spectroscopy measurements. In CRDS, laser light is directed into the cavity at one mirror and aligned to cause the light to propagate in the cavity between the mirrors in a repetitive path. Optical output at one or more mirrors is monitored with a light sensor. The laser is either pulsed or made to cease entry into the cavity after a period of time, following which the signal recorded at the light sensor is a decaying or ringdown signal, which decreases in time in a known way that is related to the concentration of gas species in the cavity.

Integrated cavity output spectroscopy (ICOS) is another gas sensing technique that can be used to measure gas concentration of species in a gas mixture. This particular technique provides an enhanced cavity sensitivity as compared to convention CRDS and uses a less complex setup than conventional CRDS. In CRDS it is generally desirable to only excite the $TEM_{00}$ mode of the laser into the cavity. This is because the transverse modes sample a greater portion of the mirror surface. Inhomogeneties in mirror reflectivity lead to variation in ringdown time constants. With ICOS, the transmitted output of the cavity is time-integrated to provide an absorption spectrum as the wavelength is scanned through the region of interest. The spectrum is then converted to absorbance through the Beer-Bougert-Lambert Law.

Other known measurement techniques are also described in U.S. Pat. No. 5,912,740 to Zare et al. and U.S. Pat. No. 6,795,190 to Paul et al., both of which are hereby incorporated herein by reference in their entirety. In the '740 patent ring-shaped resonant cavities for spectroscopy are provided which allow a reduction in optical feedback to the light source, and provide information on the interaction of both s- and p-polarized light with samples. A laser light source is locked to a single cavity mode. An intracavity acousto-optic modulator may be used to couple light into the cavity. In the '190 patent, a method is described which introduces a continuous-wave light beam into the cavity using an off-axis cavity alignment geometry to systematically eliminate the resonances commonly associated with optical cavities, while preserving the absorption signal amplifying properties of such cavities. This reduces the complexity of the apparatus considerably compared with other optical cavity-based absorption methods when applied in conjunction with either CRDS or ICOS.

SUMMARY

The '740 and '190 patents are two examples of different approaches to alternate CRDS or ICOS cavity configurations that improve on CRDS or ICOS. Embodiments of the present invention provide an alternate cavity configuration and method that includes the incorporation of a hollow waveguide into an optical cavity.

Cavity Ringdown Laser Absorption Spectroscopy (CRDS) is a measurement technique that is implemented by bouncing transverse electric modal fields of light between two mirrors of known reflectivity (and hence loss). At each pass, the medium in the open cell between the mirrors attenuates a small fraction of the light energy. The rate of attenuation is dependent on the total energy in the cavity such that the energy in the cavity has an exponential-like decay profile or "ringdown" curve. The energy in the cavity is commonly sampled over time by monitoring the loss through one of the mirrors with a high-speed detector. The ringdown temporal profile, allows one to extremely precisely determine the overall media loss (described in loss per unit length such as dB/m) between the mirrors. Depending on the particular application, this loss is subsequently commonly converted into an application-specific measurement such as concentration of a particular gas species, concentration of a scattering species such as dust, or quality of an optical design such as mirrors or optical elements. CRDS commonly deploys a tunable wavelength laser source that allows one to scan the absorption background in whatever form it may occur as a function of wavelength. In many applications, the measurement of absorption vs. wavelength uniquely identifies an absorbing constituent or characterizes the performance of a system such that the technique not only quantifies absorption, but also identifies or discriminates the source of the absorption. Given the very large number of passes (1000's) that occur during a typical CRDS measurement before a signal is completely extinguished, the CRDS measurement technique is extremely sensitive to absorption between the two highly reflective mirrors.

A hollow waveguide (HWG) is an optical structure with a hollow core(s) or hollow cross-sectional structure that can be filled with a gas, liquid, or material of differing dielectric properties than the waveguide itself. The waveguide serves to establish a discrete set of transverse electric field profiles (a.k.a. modal fields) and guides these modal fields along the axis of the waveguide (note waveguide does not necessarily need to be straight). Each modal field has its own axial modal velocity which is correlated with the angle of bounce of a geometric ray inside the waveguide. By careful design of the waveguide, light can be made to propagate axially along the waveguide with low attenuation losses of the modal fields. Two fundamental energy dissipative losses of the modal fields exist in the HWG: 1) Radial transmission through the "leaky" waveguide into the surrounding environment; and 2) Absorption losses in the waveguide itself and hollow core (when filled with an absorbing medium). By careful selection of the real and complex refractive indices of the waveguide materials and geometry, the inherent dissipative losses in the HWG can be made sufficiently small to allow cavity ringdown laser absorption spectroscopy to be conducted. The electric modal fields described herein are most commonly associated with optical wavelengths of light although waveguides can be scaled up to operate at longer wavelengths. Exemplary HWG's that have lower cavity attenuation losses (per round trip) than typical CRDS mirrors have been shown to be both theoretically and experimentally feasible. Therefore, HWG-CRDS is technically feasible.

The unique and novel hollow waveguide cavity ringdown spectroscopy (HWG-CRDS) design disclosed herein provides a substantial improvement in a number of areas associated with CRDS measurements of absorption between two CRDS mirrors and the design of a cell that contains the absorbing medium. Aspects of the invention relate to measurement of loss mechanisms in an optical cavity in general such as measurement of mirror reflectivity, measurement of attenuation by an optic element of the cell, measurement of scattering, absorption, or extinction by a gas, liquid, or solid phase suspended in the optical cell or adhered to the walls of the cell. In one embodiment, measurements of loss mechanisms in a hollow waveguide cavity correspond to at least one of liquid concentration measurements, light extinction by a liquid including mixtures and liquids adhered to a cavity mirror. In another embodiment, measurements of loss mechanisms in a hollow waveguide cavity correspond to at least one of solid concentration measurements, light extinction by a solid including aerosols, particles suspended in a gas and/or liquid, and solids adhered to a cavity mirror. In yet another embodiment, measurements of loss mechanisms in a hollow waveguide cavity correspond to loss mechanisms associated with optical elements of the optical cell including at least one of a cavity mirror, the waveguide and optical elements placed inside a cavity of the waveguide. In a further embodiment, measurements of loss mechanisms in a hollow waveguide cavity correspond to light loss mechanisms associated with at least one of holes, imperfections, particles, defects, and voids in a cavity of the waveguide. By the use of HWG-CRDS, several distinct advantages exist over conventional CRDS: 1) Sample volumes of the cell can be significantly reduced by containing the light power flow in a highly constrained volume without significantly increasing cavity losses. In such a case, much smaller samples can be analyzed such as gases evolved from highly localized regions in a precision sampled volume, 2) Light can be injected through a mirror aperture and simultaneously contained within the cavity over the entire ringdown profile. a) This configuration would enable very large enhancements in injected cavity energy drastically reducing the laser power requirements for conducting Pulsed-CRDS (P-CRDS). b) For a given laser power using P-CRDS, this configuration would significantly improve any combination of measurement sensitivity and measurement time by enhancing the Signal-to-Noise (S/N) ratio of the CRDS measurement by up to a factor of $\sim 10^4$. Pulsed-CRDS (P-CRDS) does not require precision length tuning of a cavity. 3) HWG supports mode propagation angles large enough such that precision tuning of a CRDS cavity could be conducted by altering the injection angle into the waveguide rather than mechanically tuning the cavity length. In such a case, precision length tuning of the cavity is not required. 4) HWG supports a large continuum of longitudinal modes unlike an open cell. Mode-beating behavior associated with a small set of supported modes in an open cell P-CRDS significantly limits the sensitivity of the P-CRDS measurement (particularly for long pulse lengths greater than the round-trip time of the cavity). Mode-beating behavior may be drastically attenuated by excitation of a large distribution of HWG longitudinal modes, all with different modal velocities to enhance measurement sensitivity. 5) The configuration of the CRDS mirrors with the hollow waveguide is inherently more robust to optical alignment variations particularly for low cost instrument development compared to an open cell configuration.

In conventional CRDS, laser light enters the cavity through the back of a highly reflective mirror (Reflectivity=99.9%-99.99% typical). Light transmission into the cavity at the mirror interface is described by: Transmission=1−Reflectivity; where transmission typically is 0.001 to 0.0001. Because of this typically low transmission coupling efficiency, continuous wave cavity ringdown spectroscopy (CW-CRDS) is a commonly used cavity-enhanced spectroscopy technique. CW-CRDS uses a continuous laser beam source to increase the laser energy in the cavity typically up to the point where incoming light energy balances cavity losses. At this point the laser coupling is rapidly shut-off and the ringdown profile is observed. In CW-CRDS, to couple light energy into the cavity at a particular wavelength, the transmissive cavity longitudinal mode and laser wavelength are locked to each other by both laser scanning and high precision tuning of the cavity length so that the cavity length is resonant with the longitudinal mode of excitation light. In this configuration, the overall cavity length has to be tuned to ~wavelength of light being injected into the cavity. In one embodiment of the invention, CW-CRDS can be conducted in a HWG whereby the sample volume is greatly reduced and clearly defined.

Pulsed CRDS (P-CRDS) is another version of CRDS that does not necessarily require precision tuning of the cavity. By removing the requirement for a precision tuned laser cavity at certain wavelength spatial resolutions, the overall CRDS process is simplified and the cost of producing the apparatus that supports accurate measurements of gas concentrations is reduced. In the P-CRDS configuration, the length of the laser pulse of light is commonly restricted to ~one roundtrip time of the cavity (for a 1 m cavity length this is ~6.7 nanoseconds). As a result, P-CRDS is very sensitive to coupling efficiency since cavity energy is not allowed to accumulate, but rather is limited to the energy contained in a very short pulse. P-CRDS cavity energy is fundamentally limited to the cavity mirror transmissivity. In another embodiment of the invention, the laser light is made to enter the cavity by focusing onto a small spot on the surface of one mirror. The high reflectivity coating is removed or otherwise absent at the laser focal spot, allowing the majority of the light to enter the cavity (transmission is increased up to 1.0 or up to 10,000 times greater than conventional CRDS). The waveguide contains this focused light energy whereas in conventional open cell CRDS, the light energy would be rapidly transmitted out of the cavity after a small number of mirror reflections. In this particular case, in order to minimize attenuation in the HWG, the propagation angle of excited modes may be kept shallow (<5 degrees). A trade-off in extremely shallow injection angles is the loss in reflectivity in the entrance mirror as the F/# of the focusing optic increases (and aperture size due to focus spot size subsequently increases). The HWG is designed such that axial losses are small at the injected light propagation angles where the CRDS measurement will be acquired.

In P-CRDS, the hollow waveguide allows propagation of a very large continuum of cavity modes including modes with high propagation angles, while conventional CW-CRDS allows transmission only at discrete optical frequencies limited to very low propagation angles. To overcome the discrete frequency problem of conventional cavity-enhanced spectroscopy, the cavity length is varied causing the transmissive frequencies to shift. In accordance with at least some embodiments of the present invention, this will be unnecessary as the nature of the hollow waveguide and method of light injection is to allow a near continuum of light to propagate in the cavity at very low loss. In one embodiment of the invention, a large distribution of excited modal fields of different wavelengths can be simultaneously excited in the HWG and monitored with a high speed spectrometer in order to determine a near instantaneous measurement of spectrally dependent absorption without requiring laser tuning. In such a design, the requirements on laser excitation source linewidth and tuning range are greatly reduced.

In another embodiment of the invention, the injection light is focused to excite a distribution of propagation angles. The large propagation angles of the HWG allow fixed length HWG cells to be tunable over a wide frequency range compared to the open cell CW-CRDS configuration where a very narrow band of frequencies are resonant. Since propagation constants resonant with the cavity will be magnified particularly for longer pulse lengths approaching CW-CRDS, and propagation constants consist of both the wavelength of light and the propagation angle In open cell CRDS, the mode propagation angle is very small (near 0 degrees), the actual small angle dependent on the radius of curvature of the end mirrors. Therefore, as previously discussed, to tune a longitudinal mode of light into the cavity, the wavelength of light in the cavity effectively needs to be resonant with the cavity length. In the HWG-CRDS technique, given the large propagation angles that are possible in the HWG, a longitudinal mode (combination of wavelength of light and propagation angle) must be resonant with the cavity. As such, instead of requiring the cavity length to be actively tuned, in HWG CW-CRDS, the cavity length can be passively fixed and instead the injection angle into the HWG can be precision tuned or alternatively a distribution of propagation angles can be excited by a coupling optic. For a given propagation constant that is resonant with the fixed length cavity, there will be corresponding propagation angle(s) that is(are) resonant with the cavity for a specific wavelength of light such that even a fixed length cell becomes wavelength tunable. In this case a large enough distribution of propagation angles needs to be excited to ensure there is a resonant propagation angle for any wavelength. In one embodiment of the invention, a coupling optic that modulates the injection angle (e.g. acousto-optic, thermally controlled grating, piezo-electric optical coupler) can be used to conduct CRDS or ICOS with a continuous wave laser in an HWG instead of requiring mechanical length changes of the overall cavity. In another embodiment of the invention, a coupling optic excites a large enough distribution of mode propagation angles, a very small subset of which are actually resonant with the cavity for any given wavelength. The large continuum excitation of propagation angles coupled with the selectivity of resonant modes with long pulse lengths approaching CW-CRDS in a fixed length cavity ensures that the cavity is wavelength tunable without requiring mechanical length changes of the overall cavity.

Gas is introduced in the cell by flow paths in the hollow waveguide and one or more of the mirrors, or by flow paths only in hollow waveguide, or by flow paths only in one or more of the mirrors. To design the flow paths, one must balance the entrainment rate of gas into the cavity with optical loss introduced by the flow path. Larger or more numerous flow paths will increase optical losses. Possible implementations include, but are not limited to, the following. In one implementation, the flow paths may consist of a plurality of small holes in the hollow waveguide, each hole being of smaller characteristic dimension (diameter) than the light used for gas concentration measurement in the core of the waveguide. In another implementation, the flow paths may consist of a channel through the mirror where the laser light enters the cavity. In this implementation the channel is coincident with the location of the area of removal of the high reflectivity coating. In another implementation, the flow path consists of a separation between the hollow waveguide and one or more of the mirrors. In one embodiment, an optical cell comprises a gap between a waveguide and a cavity mirror that facilitates introduction of at least one of a gas, liquid, and solid sample to a hollow waveguide cavity. In another implementation, the flow path consists of a single radial channel or multiple radial channels at the end of the hollow waveguide, the waveguide being in contact or near contact with the mirror around the majority its circumference, but for the locations of the flow paths. Other implementations include a temporary alteration of the cavity geometry to introduce gas followed by sealing of the cavity for reduction of optical losses and the gas concentration measurement. This implementation may consist of increasing the separation between the hollow waveguide and on or more of the mirrors for gas introduction, followed by sealing of the hollow waveguide against the mirror surface for gas concentration measurement.

The "IR Absorption for Biogenic Trace Gas Detection" NASA ASTID research award has advanced the state of the art of cavity designs for Cavity Ringdown Spectroscopy by HWG-CRDS. HWG-CRDS has several advantages over conventional CRDS techniques, including but not limited to:

Cavity energy is increased relative to pulse CRDS techniques.

Cavity-to-laser tuning requirements are eliminated.

The spectral spacing between cavity modes is greatly increased.

The cavity volume is significantly reduced.

The preceding is a simplified summary of the invention to provide an understanding of some aspects of the invention. This summary is neither an extensive nor exhaustive overview of the invention and its various embodiments. It is intended neither to identify key or critical elements of the invention nor to delineate the scope of the invention but to present selected concepts of the invention in a simplified form as an introduction to the more detailed description presented below. As will be appreciated, other embodiments of the invention are possible utilizing, alone or in combination, one or more of the features set forth above or described below.

DETAILED DESCRIPTION

Figure 1:
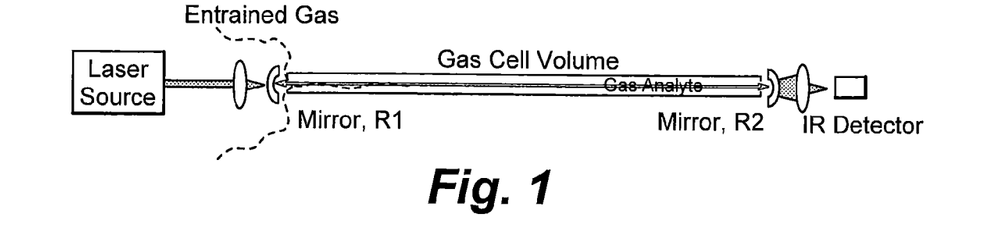
FIG. 1 is a schematic of a HWG-CRDS system used in accordance with at least some embodiments of the present invention.

Embodiments of the present invention form the unique hollow waveguide cavity ringdown spectroscopy cavity from two high reflectivity mirrors. Referring initially to FIG. 1, an exemplary HWG-CRDS system is depicted in accordance with at least some embodiments of the present invention. In CRDS an optical cell is formed by highly reflective mirrors and charged with a laser. The rate of energy decay in the cavity is monitored and related to the number density of absorbers in the cell. In conventional pulsed CRDS, light is injected into the cavity through a highly reflective mirror (R=99.9%-99.99% typical); hence most of the laser photons are not transmitted into the cavity. In the HWG-CRDS concept the cavity is formed by mirrors and a hollow waveguide. The simplified HWG-CRDS experimental arrangement shown in FIG. 1 allows the laser beam to enter the cavity through an aperture (<50 um diameter) in the reflective coating of mirror R1. The energy in the cavity is substantially increased relative to conventional pulsed CRDS with end mirrors if losses in the HWG are low. Alternatively, the light in FIG. 1 is focused in a cw-CRDS configuration through the back of a CW-CRDS to excite modes with a large distribution of propagation angles. For a given tuned wavelength, there is an available propagation angle that is resonant with the fixed length cavity. This resonant mode(s) continuously builds up its energy while other non-resonant modes are attenuated up to the point of the laser being rapidly shut-off. The HWG constrains the light propagation to travel the axial length of the waveguide (which does not necessarily need to be straight as shown). The excited modal fields subsequently propagate in the waveguide and ringdown between the two cavity mirrors allowing a very sensitive CRDS measurement to be made.

The cw-CRDS technique utilizes piezoelectric modulation of the cavity length to lock resonant cavity modes to the laser emission frequency, resulting in an increase in energy in the cavity similar to the in-cavity energy enhancement of HWG-CRDS; however, HWG-CRDS achieves this enhancement without the need for cavity length modulation. HWG-CRDS is a more simplified and robust instrument configuration than cw-CRDS. In addition, cw-CRDS can be performed only at wavelength resonant longitudinal cavity modes. The frequency spectrum can be scanned continuously with cw-CRDS by sweeping the piezoelectric element in conjunction with wavelength tuning the laser. In HWG-CRDS the frequency spacing of resonant cavity modes is dense due to the complex transverse mode structure of modes resonant in a hollow waveguide such that cavity tuning in conjunction with laser wavelength tuning is not required.

In addition, by incorporating the waveguide as the gas cell, one can simultaneously contain the light beam as well as constrain the size of the gas sample. Conventional absorption spectroscopy using a Herriot cell of 20 cm length and 2.5 cm mirror diameter would require a gas sample of 98 $cm^3$. A conventional CRDS cell of the same length would be smaller because the mirror size can be reduced as the beam is aligned to trace back and forth over the same path; for 1 cm diameter mirrors the volume would be 24 $cm^3$. We estimate that with HWG-CRDS, and a HWG designed for the 3.3 μm $CH_4$ band, the HWG diameter can be 3 mm, hence the gas volume required is reduced by greater than an order of magnitude to 2.1 $cm^3$. Reduction in required instrument gas volume reduces requirements on acquired sample volume and improves the effective spatial resolution of measurements that would locally evaporate volatiles that are concentrated in small volumes.

Figure 2:
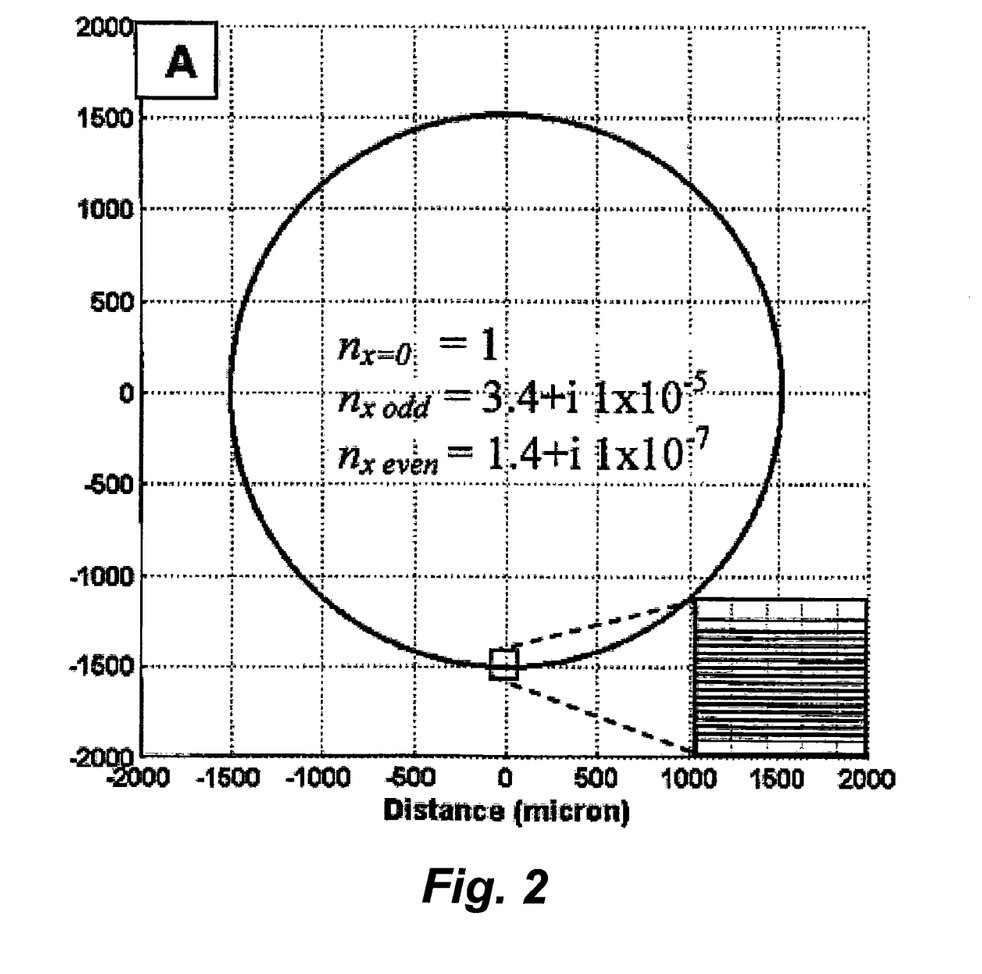
FIG. 2 is a cross-sectional depiction of a Bragg type HWG-CRDS in accordance with at least some embodiments of the present invention.
Figure 3A:
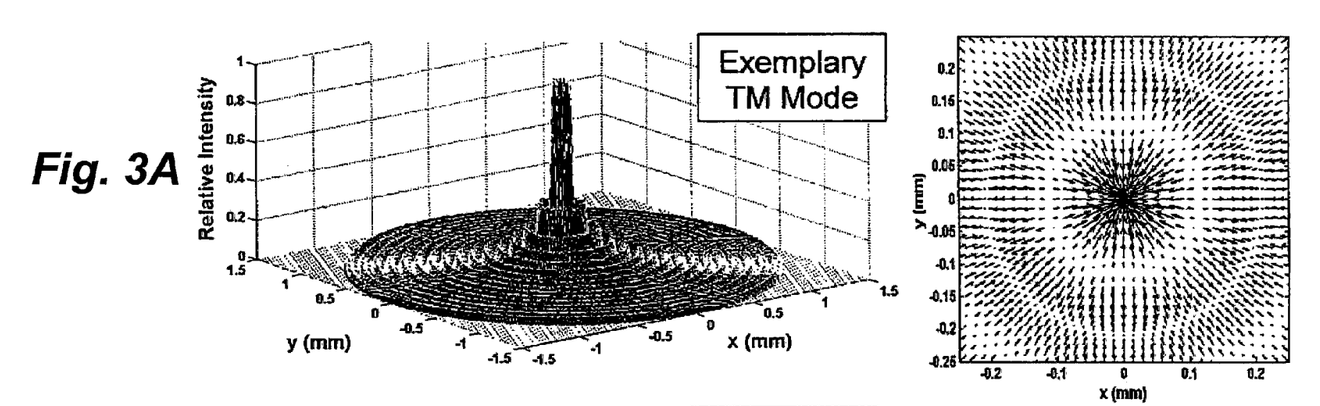
FIG. 3A illustrates an exemplary $TM_{1=0}$ modal field for a 1° mode propagation angle of a 3 mm inner diameter HWG at 3.3 micron wavelength in accordance with at least some embodiments of the present invention.
Figure 3B:
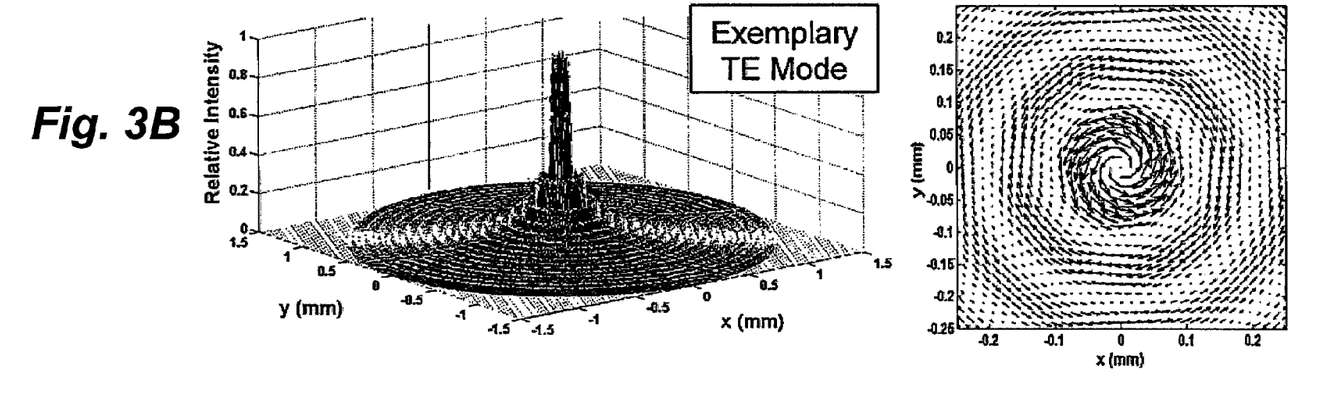
FIG. 3B illustrates an exemplary $TE_{1=0}$ modal field for a 1° mode propagation angle of a 3 mm inner diameter HWG at 3.3 micron wavelength in accordance with at least some embodiments of the present invention.
Figure 3C:
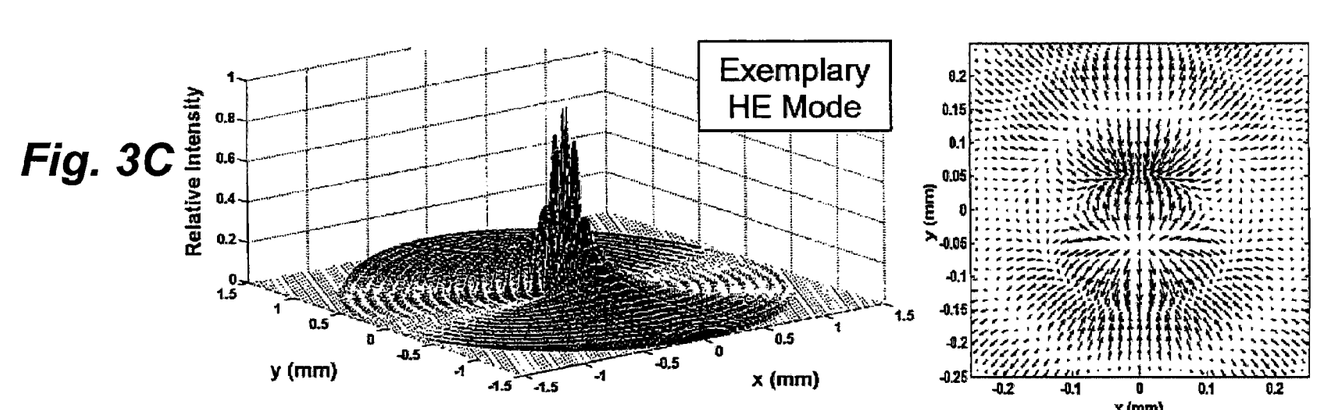
FIG. 3C illustrates an exemplary $HE_{1=1}$ modal field for a 1° mode propagation angle of a 3 mm inner diameter HWG at 3.3 micron wavelength in accordance with at least some embodiments of the present invention.
Figure 3D:
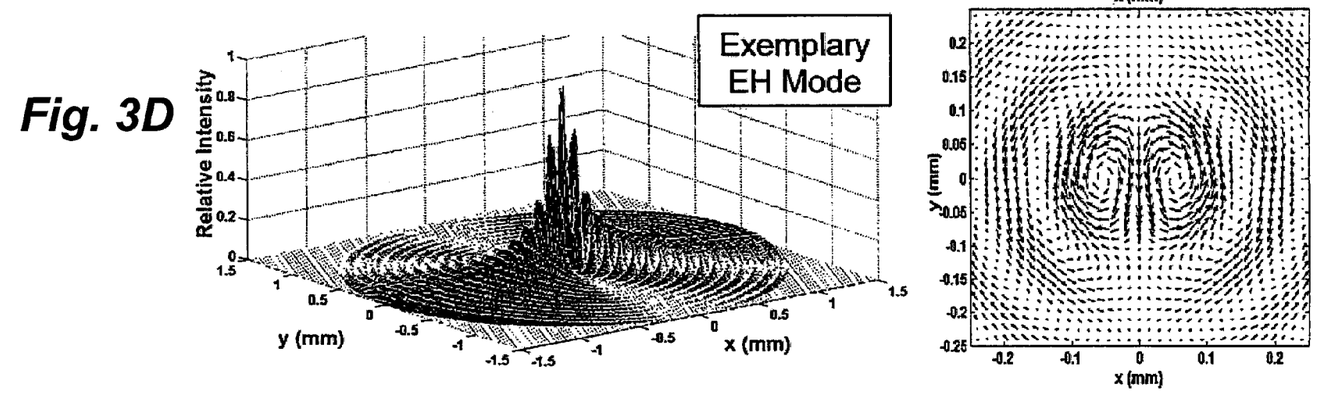
FIG. 3D illustrates an exemplary $EH_{1=1}$ modal field for a 1° mode propagation angle of a 3 mm inner diameter HWG at 3.3 micron wavelength in accordance with at least some embodiments of the present invention.

FIG. 2 illustrates a cross-sectional area of an exemplary HWG-CRDS system. The HWG may include a circular cross-section that is formed by a plurality of thin layers. Of course, other cross-sectional geometries may also be utilized. Examples of such geometries include, but are not limited to, elliptical, rectangular, triangular, square, and polygonal cross sections. In one embodiment, a hollow waveguide comprises a Bragg hollow waveguide including alternating dielectric layers surrounding a hollow core.

FIGS. 3A-D illustrate exemplary $TM_{1=0}$, $TE_{1=0}$, $HE_{1=1}$, and $EH_{1=1}$ modal fields, respectively, for a 1° mode propagation angle of 3 mm inner diameter HWG at 3.3 micron wavelength. The left column of graphs depicts the optical field relative power intensity across the full HWG inner diameter. The right column of graphs depicts transverse electric-field magnitude vector fields of the central 0.5×0.5 mm area centered on the HWG.

Four possible general field distributions (also known as polarizations) of the optical energy in a HWG-CRDS cavity are illustrated in FIGS. 3A-D. The exact distribution of energy will be dependent on transverse mode structure of the laser 104, the operation of the FMC system 116, and the coupling into the cavity such as the effects of diffraction by an aperture in the entrance mirror 120 on the modal distribution.

There are two general modes of operation envisioned with respect to modal distribution. The first is a broad spectrum modal distribution such as may be created by injecting focused linearly polarized light into a HWG. In a broad modal distribution the optical energy populates multiple TM, TE, HE, and EH modes over a range of propagation angles. In this mode of operation the HWG would be designed for low loss across a majority of these modes. In this mode of operation the requirements of the FMC system 116 could be reduced. In the second mode of operation the FMC system 116, in combination with the entrance aperture if present, would be designed to convert the laser beam to a specific range of low loss TM, TE, HE, and EH modes, The HWG would be designed in concert to have low attenuation for these populated modes.

Figure 4:
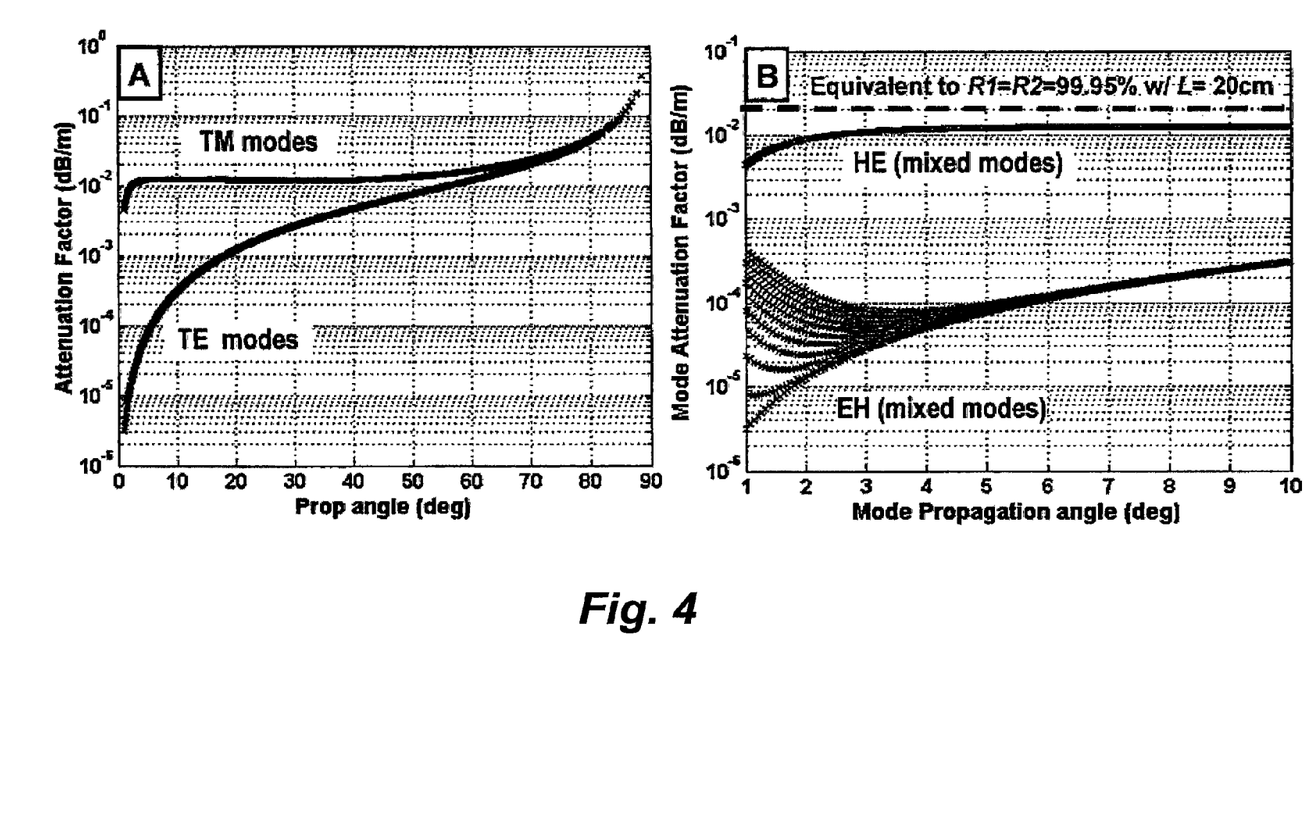
FIG. 4A is a chart depicting TE/TM bounding attenuation modes (1=0) over entire propagation angle range of HWG.
FIG. 4B is a chart depicting Modal "eigenvalues" for $1 \leq 1 \leq 10$ and shallow propagation angles.

FIG. 4 plots the complex eigenvalues for this waveguide over different effective propagation angle ranges. Note the significant lower attenuation associated with TE-like modal fields.

Figure 5:
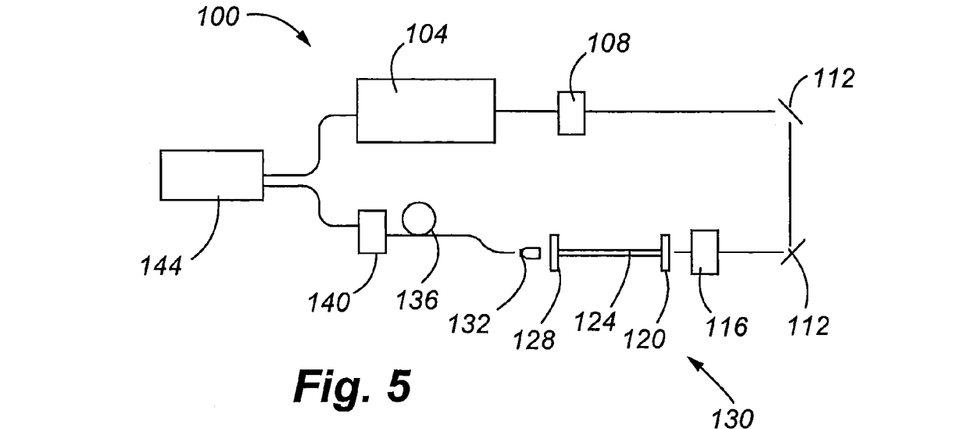
FIG. 5 is a block diagram depicting a HWG-CRDS system used in accordance with at least some embodiments of the present invention.

With reference now to FIG. 5, a HWG-CRDS system 100 will be described in accordance with at least some embodiments of the present invention. The system 100 may include a laser 104, an optical isolator 108, one or more turning mirrors 112, a focusing and transverse mode conversion optical system 116, a cavity entrance mirror 120, cavity output mirror 128, a hollow waveguide 124, a cavity output collection optic 132, an optical fiber 136, a high speed detector 140, and a high speed A/D and data acquisition computer 144. The mirrors 120, 128 and hollow waveguide 124 may correspond to an optical cell 130.

The laser 104 emits a laser beam that is directed to the focusing and mode conversion optical system 116 and the optical cell 130 by a series of turning mirrors 112. The optical isolator 108 may be included to prevent feedback to the laser 104 if needed. The laser 104 may also be directed to the optical cell 130 by other light directing means such as fiber optic delivery and the like. The laser 104 is nominally a tunable laser source such as an external cavity diode laser. An optical cavity is composed of the focusing and mode conversion optical system 116 (FMC), the optical cell 130, and the cavity output collection optic 132.

In accordance with at least one embodiment of the present invention, the focusing and mode conversion optical system 116 is nominally composed of an optic to convert the laser beam transverse mode structure to a form that is preferred low loss according to the HWG design and a focusing optic that directs the beam into the cavity with focusing according to design. By converting the mode of the laser beam before it enters the cavity the laser properties can be optimized according to the properties of the cavity. In other words, a single source laser beam may be altered in a number of different ways to accommodate a number of different cavities and gases.

The cavity entrance mirror 120 may comprise a high reflectivity mirror (on average across the HWG) that includes an aperture (that is an area or portion of the mirror with significantly reduced reflectivity as compared to the reflectivity of the rest of the mirror) that is substantially smaller than the HWG inner diameter. It should be noted that the aperture provided in the entrance mirror 120 may be any shape. In accordance with at least one embodiment of the invention, the beam is focused and aligned to the aperture such that significantly more optical energy enters the HWG than could enter if the aperture were not present and the reflectivity of this area were similar to the average reflectivity of the mirror. The cavity output is collected by an output collection optic 132 and focused into fiber 136 that delivers the optical signal to a high speed detector 140. The high speed A/D and data acquisition computer 144 then collects the optical signal and adjusts the output of the laser 104 accordingly. The data acquisition computer 144 may also provide gas absorption spectroscopy measurements as well as various attenuation coefficients related to the optical elements of the system 100.

While in one embodiment of the present invention, one of the mirrors (e.g., the entrance mirror 120) may include a small area of reflective coating removed to form an aperture, where the aperture is positioned at the center of the mirror for a hollow waveguide, other embodiments of the present invention provide that the entrance mirror 120 may not include an aperture. The aperture may also be positioned off center of the mirror surface.

The cavity ringdown signal is generated by modulation of the laser intensity. Modulation can be generated internally in many lasers by current modulation of a diode laser or pulsed operation. Modulation may also be generated externally by insertion of a mechanical chopper or acousto-optic modulator (for example) anywhere along the optical path from the laser to the entrance mirror. The equivalent effect can be achieved by modulation of the laser output wavelength such that the high density of modes in the cavity are swept intermittently, causing momentary cavity energy buildup and subsequent ringdown. Alternative embodiments of the present invention provide that the laser output can be continuous instead of being modulated and the waveguide is tuned by changing cavity length of the waveguide and/or by changing an injection angle of light into a cavity of the waveguide.

The system 100 illustrated in FIG. 5 is an exemplary hollow waveguide model design for low loss transmission of the waveguide near 1.6429 μm wavelength. The HWG is modeled as thin film layers of $SiO_2$ and $TiO_2$ coated on the inside of a quartz tube having a preferable inner diameter of about 10 mm, although other coating materials and tube materials could be used. Alternate HWGs may include photonic crystal fibers, holey fibers, or photonic-bandgap fibers, in which light is guide with low attenuation by a microstructure array of holes.

The hollow waveguide 124 may be created by coating Silica and Titania on the interior of hollow tubes. In accordance with one embodiment of the present invention, a hollow waveguide 124 may be used that comprises 30 layers total of titania and silica with a total physical thickness of about 8.7 μm. Typical refractive indices of titania and silica as produced by this method were used and have an imaginary index of the coatings can be included with a typical worst case absorption for 1.6 μm wavelength. The tube can also have a nominal finished length of about 210 mm.

Figure 7:
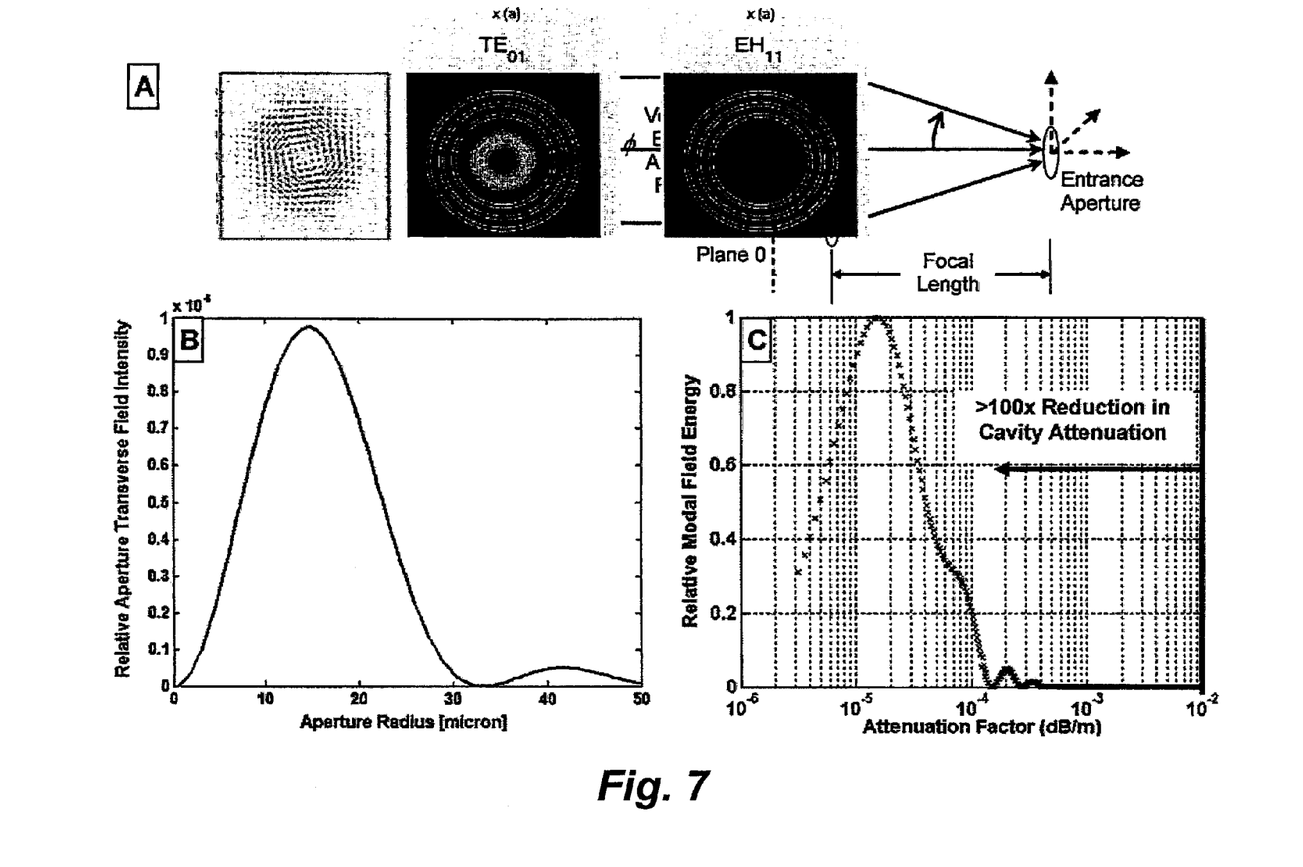
FIG. 7 is a series of charts showing a population of cavity modes when injecting an azimuthally polarized beam through a 100 micron aperture.

The HWG transverse cavity profile and dielectric properties define boundary conditions which establish what type of transverse modal fields and propagation characteristics of these modal fields can exist in an HWG. FIGS. 7A and 7B illustrate exemplary propagation characteristics of the discrete set of modal fields supported by a waveguide and examples of the electric field structure of these modal fields, respectively. In general, modal field structures that minimize electric field interactions in the absorbing structure of the waveguide have lower attenuation losses. In one embodiment of the invention, laser beams are repolarized with mode-shaping optics to excite electric modal field structure with lower corresponding attenuation losses. Lower cavity losses ultimately result in measurements with more sensitivity to the absorbing medium of interest. FIG. 7C illustrates one exemplary case of excitation of a very low loss azimuthally polarized mode by beam shaping a linearly polarized beam into an azimuthally polarized beam and injecting the beam through an aperture in one of the CRDS mirrors into the cavity. In such a case, the absorption losses in the cavity are reduced by a factor of >100.

Figure 6:
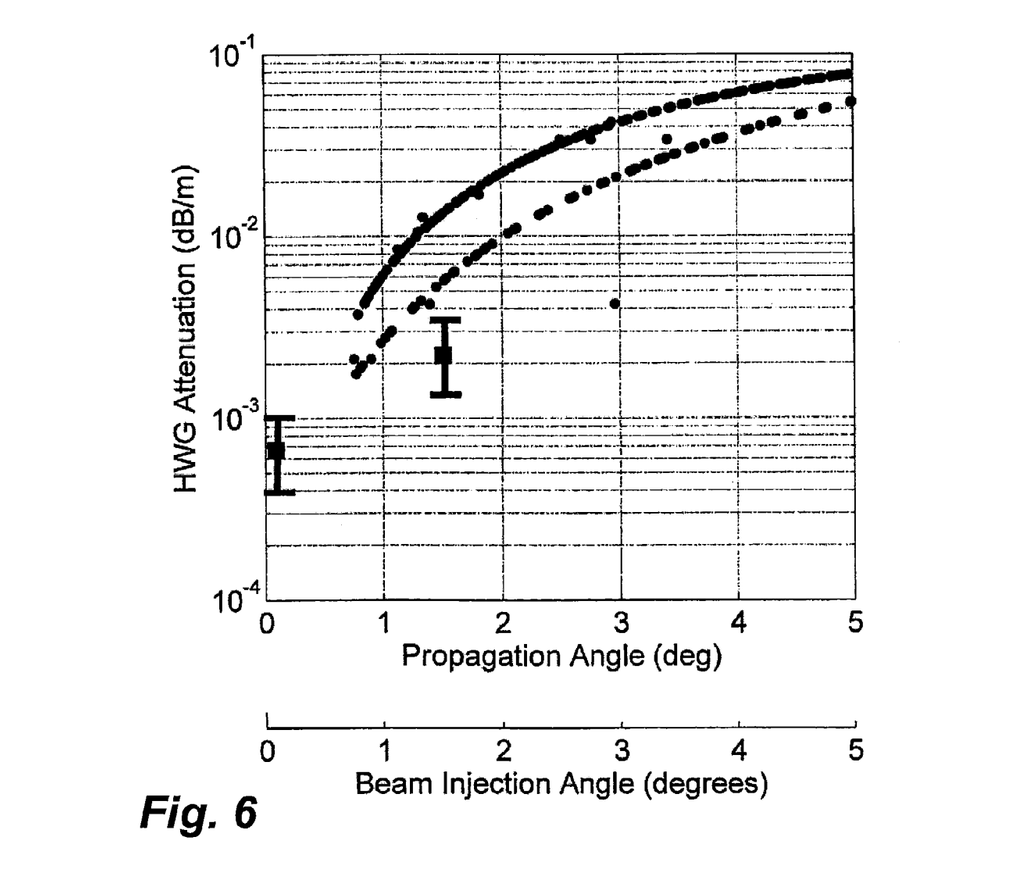
FIG. 6 illustrates an exemplary hollow waveguide model design for low loss transmission of the HWG at about 1.6429 μm wavelength in accordance with at least some embodiments of the present invention.

FIG. 6 is a chart depicting the HWG attenuation in dB/m as a function of propagation angle in deg for an exemplary hollow waveguide model design for low loss transmission of the HWG at about 1.6429 mm wavelength. The attenuation factor (solid circles) is shown at the design wavelength as a function of modal propagation angle of Transverse Magnetic (TM) corresponding to the upper line and Transverse Electric (TE) modes corresponding to the lower line of the HWG design. Experimental data points (squares with error bars) are shown as a function of Beam Injection Angle on a secondary x-axis.

The plot in FIG. 6 shows the attenuation of the HWG by two transverse modes, TE and TM modes as a function of modal propagation angle. The TM modes show greater attenuation than the TE modes. Other possible HWG designs that are possible include, but are not limited to, other thin film coatings materials, other tube materials, other tube diameters, designs that maintain mode loss at a low level over demonstrate a different range of modal propagation angles, designs for a wide wavelength range for low loss operation, designs for low loss of a very specific mode or modes.

Experimental results shown in FIG. 6 are for measured HWG attenuation at two beam injection angles. The experiment was conducted using a linearly polarized external cavity diode laser tuned to a near 1.6429 µm in a cavity of 210 mm length and HWG inner diameter of about 10 mm. Ringdown traces were recorded by rapidly modulating the laser frequency such that it swept across cavity modes, coupling a small amount of energy into the cavity on each sweep. The entrance mirror 120 did not contain an aperture in this particular series of expirements. The mirror reflectivity was measured without a waveguide using the CRDS technique. Additional cavity loss (attenuation) created by the HWG was measured at beam injection angles of about 0.1 and 1.5 degrees. A 1.5 degree beam injection angle the beam will interact with the HWG wall at least once for each round trip of the cavity. The beam propagation angle is written as a second x-axis in recognition of the nature of mode population in the HWG of the linearly polarize light use for the measurement. Linearly polarized light will populate several TM and TE modes of the HWG that are distributed over a range of propagation angles. It is not necessary to know the distribution of modes that are populated by the injected laser light, only to observe low loss consistent with making an attenuation measurement. These experimental results show that a HWG that meets the requirements of HWG-CRDS can be constructed, that the HWG-CRDS cell can be constructed, and attenuation characteristic in such a cell can be measured.

Figure 8:
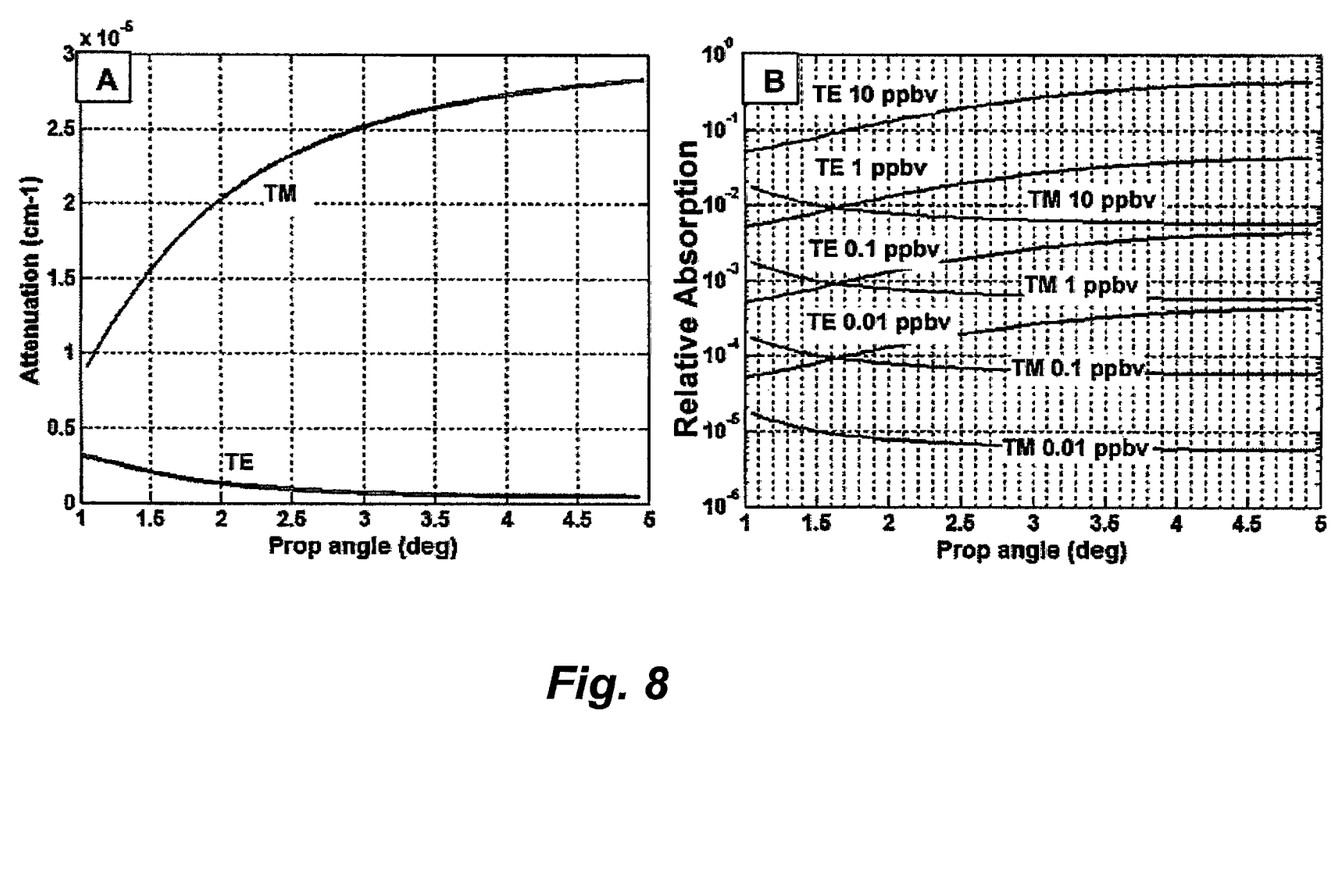
FIG. 8 illustrates a series of charts depicting absorption ($cm^{-1}$) vs. propagation angle for HWG-cavity that both empty and with trace methane at 10, 1, 0.1, 0.01 ppbv at 1=20.

For the special case of a gas-filled core, the imaginary component of index of refraction becomes a function of the volume fraction of absorbers at a particular wavelength which increases the overall cavity attenuation. FIG. 8 illustrates how the overall cavity absorption changes as function of methane concentration. Clearly, the TE-like modes in a HWG, in general provide much higher sensitivity to gas species concentrations than TM modes based on the respective relative absorption of these modes.

Figure 9:
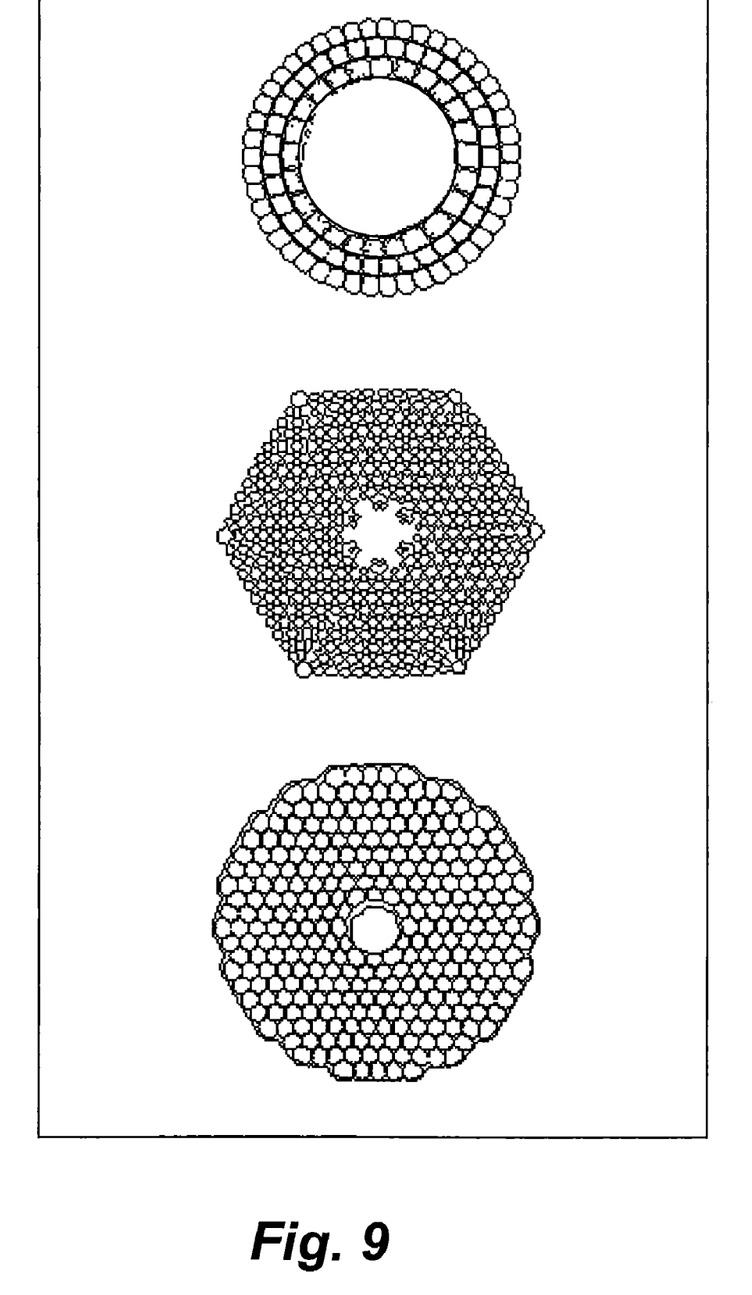
FIG. 9 illustrates exemplary waveguide structures in accordance with at least some embodiments of the present invention.

FIG. 9 illustrates a number of alternatives to a Bragg type waveguide, such as a Photonic Crystal Fiber (PCF), which is a microstructured fiber such as is available from Crystal-Fibre. These fibers generally consist of one material and an array of holes formed that would be filled with a gas. The PCF is formed by the same methods as conventional optical fiber, in that a preform of macro-sized glass tubes is drawn and fused under heating to the final design microstructure. Core diameters are typically smaller than we consider reasonable for the HWP-CRDS technique; however, cores to 120 um have been reported. Crystal-Fibre has indicated that larger diameters are possible as it is a mater of stopping the drawdown at the right time. The gas entrained for sensing fills the micro-gaps as well as the core; hence the entire "holey" area will also be active in gas absorption. The PCF in HWP-CRDS may exhibit unique properties. Gas sensing with PCF has been shown, but to our knowledge, gas sensing in a high finesse PCF cavity has not been attempted. Predictive model development: we believe the Bragg model can be used to predict behavior of these PCF microstructure arrays using circularly symmetric layers of alternating layers of glass and gas to approximate the PCF structure.

EXAMPLE

A HWG for use at 1.66 µm was designed and manufactured. The 1.66 µm HWG allowed measurements of $CH_4$ on the $2v_3$ overtone absorption band. An external cavity tunable diode laser, Sacher Lasertechnik Lion Laser (TEMTEC-500-1630-31650) was used with internal piezoelectric modulation of the laser frequency at 1 kHz. The piezoelectric tuning was set to sweep through approximately one free spectral range of an open cell cavity longitudinal mode of the length of the hollow waveguide cavity. A small portion of the laser energy was sampled and directed to a wavemeter (Bristol 621A-NIR), which recorded the average laser frequency at a rate of 4 Hz, using a 20× microscope objective and a single mode fiber. The TEC laser operated in the range of 1573-1675 nm with peak output power >3 mW and bandwidth <5 MHz (20s) and typically <0.5 MHz (50 ms).

The laser beam was directed by free space optics and focused into the cavity. The cavity was formed by two Newport Ultra-Low Loss SuperMirrors™ (10CM00SR10CV00SR.70F, 1 m ROC) in kinematic rear mounting mirror mounts. Manufacturer data states the mirror finesse is >10,000, and reflectivity >99.97%, from 1457-1659 nm. Open cell ringdown measurements using two mirrors in a dry N2 atmosphere produced a mean reflectivity of 99.976% at 1640 nm per mirror, assuming the reflectivity of the two mirrors used was identical. A custom fitting was mounted to the mirror mount to hold the HWG to the face of the mirrors and seal the gas cell to room air. The gas in the cell could be exchanged and flow through the cell from either end. The HWG was the 1.66 µm multi-layer waveguide described previously. For open cell measurements (conventional CRDS) the HWG was replaced with a brass tube of 7/16 inch inner diameter.

Output from the cavity was collected by a 10× microscope objective and focused into a low OH Vis-IR optical fiber (ThorLabs AFS105/125Y). The fiber core diameter was 105 mm, NA 0.22, length used <1 m. The fiber was connected to a high speed photodiode detector (New Focus Model 2053). The detector has adjustable gain and frequency cut off settings. Ringdown measurements were typically made with the detector set on gain of 300 or less, high frequency cut off frequency of 3 MHz or higher, and low frequency cut off at dc. The HWG-CRDS output signal and laser piezoelectric sync signal were recorded by a data acquisition computer using high speed data acquisition board (Gage, 200 MS/s, 16 bit resolution). Typical acquisition rates on the acquisition board were set at 50 MS/s as this was sufficient given the slower detector cut off frequency.

Ringdown was achieved by careful translational alignment of the laser beam to the cavity followed by alignment of first the second cavity mirror (output end) back reflection to come back on the beam, and then the first cavity mirror (input end) back reflection to come back on the input beam. After this alignment further adjustment of mirror tilt was normally unnecessary to observe the build up and subsequent ringdown of the cavity as the cavity and laser modes became coincident. The cavity length as not modulated by piezo electric transducer as is common in cw-CRDS experiment. The laser frequency was modulated by a piezo electric transducer internal to the laser cavity. The piezo modulation was adjusted such that the laser frequency would consistently sweep across cavity modes, generally this was set to ½ to 1 open cell FSR. The amplitude of piezo modulation was measured using the wavemeter with piezo modulation at low frequency (0.1 Hz). Piezo modulation for ringdown experiments were performed at 1 kHz using a triangular modulation function. Given the rate of change in frequency from modulation, the laser line width (typical 50 ms linewidth), and estimated cavity mode width, the rate at which the laser swept across modes was less than 2 ns.

What is claimed is:

1. A method, comprising:
  defining an optical cell with a linear hollow waveguide cavity; and
  conducting cavity ringdown absorption spectroscopy for measurements of loss mechanisms in the linear hollow waveguide cavity, wherein light energy for exciting the linear hollow waveguide cavity is introduced into the linear hollow waveguide cavity through a back of a cavity mirror positioned at an end of a linear hollow waveguide.

2. The method of claim 1, wherein measurements of loss mechanisms in the hollow waveguide cavity correspond to at least one of gas concentration measurements and light extinction by a gas.

3. The method of claim 1, wherein measurements of loss mechanisms in the hollow waveguide cavity correspond to at least one of liquid concentration measurements, light extinction by a liquid including mixtures and liquids adhered to the cavity mirror or the linear hollow waveguide.

4. The method of claim 1, wherein measurements of loss mechanisms in the hollow waveguide cavity correspond to at least one of solid concentration measurements, light extinction by a solid including aerosols, particles suspended in a gas and/or liquid, and solids adhered to the cavity mirror or the linear hollow waveguide.

5. The method of claim 1, wherein measurements of loss mechanisms in the hollow waveguide cavity correspond to loss mechanisms associated with optical elements of the optical cell including at least one of the cavity mirror, the waveguide and optical elements placed inside a cavity of the waveguide.

6. The method of claim 1, wherein measurements of loss mechanisms in the hollow waveguide cavity correspond to light loss mechanisms associated with at least one of holes, imperfections, particles, defects, and voids in a cavity of the waveguide.

7. The method of claim 1, wherein the hollow waveguide comprises a low attenuation loss waveguide that is adapted to entrain at least one of a gas, liquid, and solid sample and wherein the optical cell comprises holes in the waveguide, the cavity mirror, and/or gaps between the waveguide and the cavity mirror that facilitate introduction of the at least one of a gas, liquid, and solid sample to the hollow waveguide cavity.

8. The method of claim 1, wherein the hollow waveguide comprises a Bragg hollow waveguide including alternating dielectric layers surrounding a hollow core.

9. The method of claim 1, wherein the hollow waveguide comprises a photonic bandgap waveguide.

10. The method of claim 1, wherein the hollow waveguide comprises a photonic crystal waveguide.

11. The method of claim 1, further comprising using a transverse mode converter to generate and couple lower attenuation loss modes and modal fields into the hollow waveguide cavity.

12. The method of claim 1, wherein a pulsed laser is used to excite cavity modes.

13. The method of claim 1, wherein a continuous laser is used to excite cavity modes.

14. The method of claim 1, wherein the hollow waveguide cavity is tuned by changing a cavity length of the linear hollow waveguide.

15. The method of claim 1, wherein the hollow waveguide cavity is tuned by changing an injection angle of light into the hollow waveguide cavity or by focusing injection light to excite a distribution of modal propagation angles that have a corresponding wavelength that is resonant with the cavity.

16. The method of claim 1, wherein light energy for exciting the cavity is focused through an aperture in the cavity mirror positioned at the end of the linear hollow waveguide.

17. The method of claim 16, wherein the aperture comprises a portion of the mirror with a reduced reflectivity as compared to a reflectivity of a remainder of the mirror, the aperture is less than 50 μm in diameter, and the aperture is positioned at a center of a surface of the mirror.

18. A cavity ringdown spectroscopy system, comprising:
  an optical cell including a straight path hollow waveguide positioned between two mirrors, the two mirrors configured to reflect light between one another within the straight path hollow waveguide, wherein the optical cell is configured to conduct cavity ringdown absorption spectroscopy for measurements of loss mechanisms within the straight path hollow waveguide.

19. The system of claim 18, wherein the straight path hollow waveguide comprises a Bragg hollow waveguide including alternating dielectric layers surrounding a hollow core and wherein measurements of loss mechanisms within the straight path hollow waveguide correspond to gas concentration measurements.

20. The system of claim 18, further comprising a transverse mode converter to match an optical source to modes defined by the straight path hollow waveguide.

21. The system of claim 18, wherein the optical cell includes a plurality of straight path hollow waveguides defined in a single microstructured fiber, wherein each of the plurality of straight path hollow waveguides defined in the single microstructured fiber are configured to conduct cavity ringdown absorption spectroscopy therein.

22. The system of claim 18, wherein one of the mirrors has an aperture that is substantially smaller than an inner diameter of the hollow waveguide.

23. The system of claim 22, wherein the aperture comprises a portion of the mirror with a reduced reflectivity as compared to a reflectivity of a remainder of the mirror, the aperture is less than 50 μm in diameter, and the aperture is positioned at a center of a surface of the mirror.

* * * * *